US012351552B2

(12) United States Patent
Luo et al.

(10) Patent No.: US 12,351,552 B2
(45) Date of Patent: Jul. 8, 2025

(54) METHODS FOR PRODUCING OLEFINS

(71) Applicant: Dow Global Technologies LLC, Midland, MI (US)

(72) Inventors: Lin Luo, Lake Jackson, TX (US); Yang Yang, Freeport, TX (US); Adrianus Koeken, Terneuzen (NL); Brien Stears, Seabrook, TX (US); Luis Bollmann, Freeport, TX (US); Andrzej Malek, Midland, MI (US); Brian W. Goodfellow, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 136 days.

(21) Appl. No.: 18/257,895

(22) PCT Filed: Dec. 15, 2021

(86) PCT No.: PCT/US2021/063489
§ 371 (c)(1),
(2) Date: Jun. 16, 2023

(87) PCT Pub. No.: WO2022/132884
PCT Pub. Date: Jun. 23, 2022

(65) Prior Publication Data
US 2024/0051901 A1    Feb. 15, 2024

Related U.S. Application Data

(60) Provisional application No. 63/127,465, filed on Dec. 18, 2020.

(51) Int. Cl.
*C07C 5/333*    (2006.01)
*B01J 21/04*    (2006.01)
(Continued)

(52) U.S. Cl.
CPC .............. *C07C 5/3337* (2013.01); *B01J 21/04* (2013.01); *B01J 23/62* (2013.01); *B01J 23/96* (2013.01);
(Continued)

(58) Field of Classification Search
CPC .............. C07C 5/3337; C07C 2523/62; C07C 5/3335; C07C 11/06; B01J 21/04;
(Continued)

(56) References Cited

U.S. PATENT DOCUMENTS 2,459,444 A    1/1949  Main
4,225,531 A    9/1980  Jones et al.
(Continued)

FOREIGN PATENT DOCUMENTS

WO    2013126210 A1    8/2013
WO    2020006270 A2    1/2020
(Continued)

OTHER PUBLICATIONS

International Search Report and Written Opinion dated Apr. 4, 2022, pertaining to Int'l Patent Application No. PCT/US2021/063489.
(Continued)

*Primary Examiner* — Ali Z Fadhel
(74) *Attorney, Agent, or Firm* — Dinsmore & Shohl LLP

(57)    ABSTRACT

According to one or more embodiments of the present disclosure, a method for producing olefins includes contacting a hydrocarbon-containing feed with a catalyst in a reactor portion of a reactor system to form an olefin-containing effluent, separating at least a portion of the olefin-containing effluent from the catalyst, passing the catalyst to a catalyst-processing portion of the reactor system and processing the catalyst to produce a processed catalyst and a combustion gas, passing the processed catalyst from the catalyst-processing portion to the reactor
(Continued)

portion, and introducing a combustion additive to the reactor system when the combustion gas comprises one or more hydrocarbons in an amount greater than 5% of an LFL of the combustion gas at a temperature and pressure of the catalyst processing portion. The catalyst may include from 1 ppmw to 150 ppmw platinum. The combustion additive may include from 150 ppmw to 1,000 ppmw platinum.

15 Claims, 1 Drawing Sheet

(51) Int. Cl.
  *B01J 23/62* (2006.01)
  *B01J 23/96* (2006.01)
  *B01J 38/02* (2006.01)
  *B01J 38/30* (2006.01)
(52) U.S. Cl.
  CPC .............. *B01J 38/02* (2013.01); *B01J 38/30* (2013.01); *C07C 2523/62* (2013.01)
(58) Field of Classification Search
  CPC ............ B01J 23/62; B01J 23/96; B01J 38/02; B01J 38/30; Y02P 20/52; Y02P 20/584
  See application file for complete search history.

(56) References Cited

U.S. PATENT DOCUMENTS

| | | | |
|---|---|---|---|
| 7,473,668 B2 | 1/2009 | Bartolini et al. | |
| 7,959,792 B2 * | 6/2011 | Vaarkamp | B01J 35/613 |
| | | | 208/113 |
| 9,815,040 B2 | 11/2017 | Pretz et al. | |
| 9,827,543 B2 | 11/2017 | Pretz et al. | |
| 9,834,496 B2 | 12/2017 | Pretz et al. | |
| 10,646,854 B2 | 5/2020 | Iezzi et al. | |
| 2014/0371501 A1 | 12/2014 | Luo et al. | |

FOREIGN PATENT DOCUMENTS

| | | |
|---|---|---|
| WO | 2020009860 A1 | 1/2020 |
| WO | 2020009863 A1 | 1/2020 |

OTHER PUBLICATIONS

International Search Report and Written Opinion dated Apr. 4, 2022, pertaining to Int'l Patent Application No. PCT/US2021/063481.
International Search Report and Written Opinion dated Apr. 5, 2022, pertaining to Int'l Patent Application No. PCT/US2021/063480.
Zabetakis, "Flammability Characteristics of Combustible Gases and Vapors", 627 Bureau of Mines (1965).
Coward et al., "Limits of Flammability of Gases and Vapors", 503 Bureau of Mines (1952).
Marceau et al., Impregnation and Drying, Synthesis of Solid Catalysts 59 (2008).
Cocco et al., Jet Cup Attrition Testing, 200 Powder Technology 224 (2010).
Smoothflow™ FCC additive—The solution for FCC fluidization and circulation problems https://www.albemarle.com/storage/wysiwyg/mib-smoothflow-final.pdf.
Substantive Examination dated Apr. 17, 2024, pertaining to SA Patent Application No. 523441146, 12 pgs.
Marceau et al. "Impregnation and Drying", Synthesis of Solid Catalysts, pp. 59-78 (2009).
Abstract for "Additives Play Important Role in FCC Development", Oil and Gas Journal, Oct. 2012.
Abrahamsen et al. "Behavior of Gas-Fluidized Beds of Fine Powders: Part I. Homogeneous Expansion", Powder Technology, 1980, 26, pp. 35-46.
Abrahamsen et al. "Behavior of Gas-Fluidized Beds of Fine Powders: Part II. Voidage of the Dese Phase in Bubbling Beds", Powder Technology, 1980, 26, pp. 47-55.
Mott "Troubleshooting FCC Standpipe Flow Problems", Catalagram 106, 2009, pp. 11-20.
Russian Examination and Search Report dated Apr. 18, 2025, pertaining to RU Patent Application No. RU2023118434, 18 pgs.

* cited by examiner

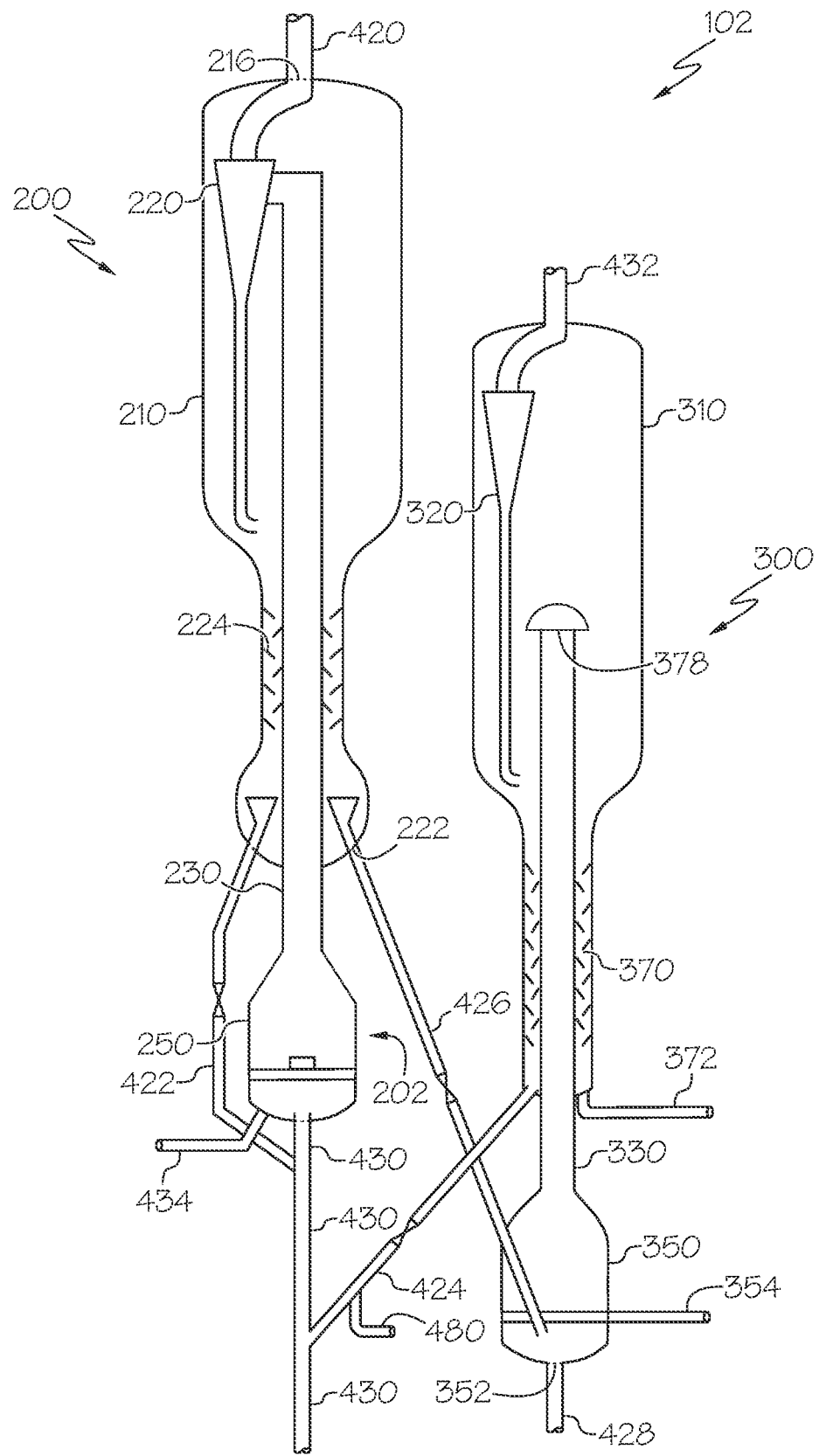

METHODS FOR PRODUCING OLEFINS

CROSS-REFERENCE TO RELATED APPLICATIONS

The present application is a National Phase Entry under 35 U.S.C. § 371 of International Patent Application No. PCT/US2021/063489 filed Dec. 15, 2021, which claims priority to U.S. Provisional Patent Application No. 63/127,465 filed Dec. 18, 2020, the entireties of both of which are incorporated by reference herein.

BACKGROUND

Field

The present disclosure generally relates to chemical processing and, more specifically, catalyst systems and methods for producing olefins using the same.

Technical Background

Light olefins, such as ethylene, may be used as base materials to produce many different materials, such as polyethylene, vinyl chloride, and ethylene oxide, which may be used in product packaging, construction, and textiles. As a result of this utility, there is a worldwide increasing demand for light olefins. Suitable processes for producing light olefins generally depend on the given chemical feed and include, for example, fluidized catalytic dehydrogenation (FCDh) processes.

SUMMARY

Generally, in FCDh processes, a hydrocarbon-containing feed and a fluidized catalyst are introduced into a reactor portion of an FCDh system, the hydrocarbon-containing feed contacts the catalyst, and the resulting mixture flows through the reactor portion to produce an olefin-containing effluent via dehydrogenation. The catalyst may be separated from the olefin-containing effluent and passed to a catalyst-processing portion of the FCDh system. Typically, the heat necessary for dehydrogenation in FCDh processes is primarily provided by the combustion of a combustion fuel, such as coke deposited on the catalyst and/or a supplemental fuel, in the catalyst-processing portion. Specifically, catalyst that has been heated by the combustion of the combustion fuel in the catalyst-processing portion transfers heat to the reactor portion. In order to combust the combustion fuel at reasonable temperatures, the catalyst is relied upon to provide combustion activity. However, the combustion activity of the catalyst will typically decrease at a rate greater than the dehydrogenation activity as the catalyst is cycled through the FCDh system. As a result, fresh catalyst must be added to the FCDh system at a rate greater than necessary to maintain sufficient dehydrogenation activity in the reactor portion in order to maintain sufficient combustion activity in the catalyst-processing portion, which greatly increases the economic cost of the FCDh process. However, the catalyst systems and methods for producing olefins of the present disclosure may efficiently maintain a sufficient combustion activity in a catalyst-processing portion of an FCDh system without significantly increasing economic cost. This is accomplished, at least in part, by the utilization of both a catalyst and a combustion additive.

According to one or more embodiments of the present disclosure, a method for producing olefins includes contacting a hydrocarbon-containing feed with a catalyst in a reactor portion of a reactor system to form an olefin-containing effluent, separating at least a portion of the olefin-containing effluent from the catalyst, passing the catalyst to a catalyst processing portion of the reactor system and processing the catalyst to produce a processed catalyst and a combustion gas, passing the processed catalyst from the catalyst processing portion to the reactor portion, and introducing a combustion additive to the reactor system when the combustion gas comprises one or more hydrocarbons in an amount greater than 5 percent (%) of a lower flammability limit (LFL) of the combustion gas at a temperature and pressure of the catalyst processing portion. The catalyst may include from 1 parts per million by weight (ppmw) to 150 ppmw platinum. The combustion additive may include from 150 ppmw to 1,000 ppmw platinum.

It is to be understood that both the preceding general description and the following detailed description describe various embodiments and are intended to provide an overview or framework for understanding the nature and character of the claimed subject matter. Additional features and advantages of the embodiments will be set forth in the detailed description and, in part, will be readily apparent to persons of ordinary skill in the art from that description, which includes the accompanying drawing and claims, or recognized by practicing the described embodiments. The drawing is included to provide a further understanding of the embodiments and, together with the detailed description, serves to explain the principles and operations of the claimed subject matter. However, the embodiment depicted in the drawing is illustrative and exemplary in nature, and not intended to limit the claimed subject matter.

BRIEF DESCRIPTION OF THE DRAWINGS

The following detailed description may be better understood when read in conjunction with the following drawing, in which:

FIG. 1 schematically depicts a reactor system, according to one or more embodiments of the present disclosure.

When describing the simplified schematic illustration of FIG. 1, the numerous valves, temperature sensors, electronic controllers, and the like, which may be used and are well known to a person of ordinary skill in the art, are not included. Further, accompanying components that are often included in such reactor systems, such as air supplies, heat exchangers, surge tanks, and the like are also not included. However, it should be understood that these components are within the scope of the present disclosure.

Reference will now be made in greater detail to various embodiments, some of which are illustrated in the accompanying drawing.

DETAILED DESCRIPTION

The present disclosure is directed to catalyst systems and methods for producing olefins using the same. More specifically, the present disclosure is directed to catalyst systems useful for dehydrogenation and methods for producing olefins via FCDh processes using the same. As discussed previously, the heat necessary for dehydrogenation in FCDh processes is primarily provided by the combustion of a combustion fuel, such as coke deposited on the catalyst and/or a supplemental fuel, in a catalyst-processing portion of an FCDh system. In order to combust the combustion fuel at reasonable temperatures, the catalyst is relied upon to provide combustion activity. However, the combustion activity of the catalyst will typically decrease at a rate greater than the dehydrogenation activity as the catalyst is cycled through the FCDh system. As a result, fresh catalyst must be added to the FCDh system at a rate greater than necessary to maintain sufficient dehydrogenation activity in the reactor portion in order to maintain sufficient combustion activity in the catalyst-processing portion, which greatly increases the economic cost of the FCDh process. However, the catalyst systems and methods for producing olefins of the present disclosure may efficiently maintain a sufficient combustion activity in a catalyst-processing portion of an FCDh system without significantly increasing economic cost. This is accomplished, at least in part, by the utilization of both a catalyst and a combustion additive.

As used in the present disclosure, the term "fluidized reactor system" refers to a reactor system in which one or more reactants are contacted with a catalyst in a fluidization regime, such as bubbling regime, slug flow regime, turbulent regime, fast fluidization regime, pneumatic conveying regime, or combinations of these, in different portions of the system. For example, in a fluidized reactor system, a chemical feed containing one or more reactants may be contacted with the circulating catalyst at an operating temperature to conduct a continuous reaction to produce an effluent.

As used in the present disclosure, the term "deactivated catalyst" refers to a catalyst having decreased catalytic activity resulting from buildup of coke and/or loss of catalyst active sites. The terms "catalytic activity" and "catalyst activity" refer to the degree to which the catalyst is able to catalyze the reactions conducted in the reactor system.

As used in the present disclosure, the terms "catalyst reactivation" and "reactivating the catalyst" refer to processing the deactivated catalyst to restore at least a portion of the catalyst activity to produce a reactivated catalyst. The deactivated catalyst may be reactivated by, but not limited to, recovering catalyst acidity, oxidizing the catalyst, other reactivation process, or combinations thereof.

The catalyst systems and methods for producing olefins of the present disclosure will now be described in the context of an example FCDh system. It should be understood that the schematic diagram of FIG. 1 is only an example system and that other FCDh systems are contemplated as well, and the concepts described may be utilized in such alternate systems. For example, the concepts described may be equally applied to other systems with alternate reactor units and regeneration units, such as those that operate under non-fluidized conditions or are downers rather than risers. Additionally, the presently described catalyst systems and methods for producing olefins should not be limited only to embodiments for reactor systems designed to produce light olefins through FCDh processes, such as the reactor system described with respect to FIG. 1, as other dehydrogenation systems (e.g., utilizing different chemical feeds) are contemplated.

Referring now to FIG. 1, an example reactor system 102 is schematically depicted. The reactor system 102 generally includes a reactor portion 200 and a catalyst-processing portion 300. As used in the context of FIG. 1, the reactor portion 200 refers to the portion of the reactor system 102 in which the major process reaction takes place. For example, the reactor system 102 may be an FCDh system in which a hydrocarbon-containing feed is dehydrogenated in the presence of a dehydrogenation catalyst in the reactor portion 200 of the reactor system 102. The reactor portion 200 generally includes a reactor 202, which may include an upstream reactor section 250, a downstream reactor section 230, and a catalyst separation section 210, which serves to separate catalyst from effluent produced in the reactor 202.

Similarly, as used in the context of FIG. 1, the catalyst-processing portion 300 refers to the portion of the reactor system 102 in which catalyst is processed in some way, such as removal of coke deposits, heating, reactivating, or combinations of these. The catalyst-processing portion 300 generally includes a combustor 350, a riser 330, a catalyst separation section 310, and an oxygen treatment zone 370. The combustor 350 may be in fluid communication with the riser 330. The combustor 350 may also be in fluid communication with the catalyst separation section 210 via standpipe 426, which may supply deactivated catalyst from the reactor portion 200 to the catalyst processing portion 300 for catalyst processing (e.g., coke removal, heating, reactivating, etc.). The oxygen treatment zone 370 may be in fluid communication with the upstream reactor section 250 (e.g., via standpipe 424 and transport riser 430), which may supply processed catalyst from the catalyst processing portion 300 back to the reactor portion 200. The combustor 350 may include one or more lower combustor inlet ports 352 where air inlet 428 connects to the combustor 350. The air inlet 428 may supply air and/or other reactive gases, such as an oxygen-containing gas to the combustor 350. The combustor 350 may also include a fuel inlet 354, which may supply a fuel, such as a hydrocarbon stream, to the combustor 350. The oxygen treatment zone 370 may include an oxygen-containing gas inlet 372, which may supply an oxygen-containing gas to the oxygen treatment zone 370 for oxygen treatment of the catalyst.

Referring still to FIG. 1, general operation of the reactor system 102 to conduct a dehydrogenation reaction under normal operating conditions will be described. During operation of the reactor portion 200 of the reactor system 102, a hydrocarbon-containing feed may enter the reactor portion 200 via feed inlet 434 and contact a fluidized catalyst introduced to the reactor portion 200 via a transport riser 430 and an olefin-containing effluent may exit the reactor portion 200 via pipe 420. In one or more embodiments, the hydrocarbon-containing feed and a fluidized catalyst are introduced into the upstream reactor section 250, the hydrocarbon-containing feed contacts the catalyst in the upstream reactor section 250, and the resulting mixture flows upwardly into and through the downstream reactor section 230 to produce the olefin-containing effluents.

In one or more embodiments, the hydrocarbon-containing feed includes ethane, propane, n-butane, i-butane, ethylbenzene, or combinations of these. In some embodiments, the hydrocarbon-containing feed includes at least 50 weight percent (wt. %), at least 60 wt. %, at least 70 wt. %, at least 80 wt. %, at least 90 wt. %, at least 95 wt. %, or at least 99 wt. % ethane. In some embodiments, the hydrocarbon-containing feed includes at least 50 wt. %, at least 60 wt. %, at least 70 wt. %, at least 80 wt. %, at least 90 wt. %, at least 95 wt. %, or at least 99 wt. % propane. In some embodiments, the hydrocarbon-containing feed includes at least 50 wt. %, at least 60 wt. %, at least 70 wt. %, at least 80 wt. %, at least 90 wt. %, at least 95 wt. %, or at least 99 wt. % of n-butane. In some embodiments, the hydrocarbon-containing feed includes at least 50 wt. %, at least 60 wt. %, at least 70 wt. %, at least 80 wt. %, at least 90 wt. %, at least 95 wt. %, or at least 99 wt. % of i-butane. In some embodiments, the hydrocarbon-containing feed includes at least 50 wt. %, at least 60 wt. %, at least 70 wt. %, at least 80 wt. %, at least 90 wt. %, at least 95 wt. %, or at least 99 wt. % of ethylbenzene. In some embodiments, the hydrocarbon-containing feed includes at least 50 wt. %, at least 60 wt. %, at least 70 wt. %, at least 80 wt. %, at least 90 wt. %, at least 95 wt. %, or at least 99 wt. % of the sum of ethane, propane, n-butane, i-butane, and ethylbenzene.

In one or more embodiments, the olefin-containing effluent includes light olefins. As used in the present disclosure, the term "light olefins" refers to one or more of ethylene, propylene, and butene. The term butene includes any isomers of butene, such as a-butylene, cis-P-butylene, trans-P-butylene, and isobutylene. In some embodiments, the olefin-containing effluent includes at least 25 wt. % light olefins based on the total weight of the olefin-containing effluent. For example, the olefin-containing effluent may include at least 35 wt. % light olefins, at least 45 wt. % light olefins, at least 55 wt. % light olefins, at least 65 wt. % light olefins, or at least 75 wt. % light olefins based on the total weight of the olefin-containing effluent.

In one or more embodiments, the catalyst includes catalytically active particles. In some embodiments, the catalyst includes one or more of gallium, platinum, alkali metals, alkaline earth metals, and a support material.

In one or more embodiments, the catalyst includes from 1 ppmw to 150 ppmw platinum based on the total weight of the catalyst. For example, the catalyst may include from 1 ppmw to 100 ppmw, from 1 ppmw to 50 ppmw, from 1 ppmw to 25 ppmw, from 1 ppmw to 15 ppmw, from 1 ppmw to 5 ppmw, from 5 ppmw to 150 ppmw, from 5 ppmw to 100 ppmw, from 5 ppmw to 50 ppmw, from 5 ppmw to 25 ppmw, from 5 ppmw to 15 ppmw, from 15 ppmw to 150 ppmw, from 15 ppmw to 100 ppmw, from 15 ppmw to 50 ppmw, from 15 ppmw to 25 ppmw, from 25 ppmw to 150 ppmw, from 25 ppmw to 100 ppmw, from 25 ppmw to 50 ppmw, from 50 ppmw to 150 ppmw, from 50 ppmw to 100 ppmw, or from 100 ppmw to 150 ppmw platinum based on the total weight of the catalyst.

In one or more embodiments, the catalyst includes from 0.1 wt. % to 10.0 wt. % gallium based on the total weight of the catalyst. For example, the catalyst may include from 0.1 wt. % to 7.5 wt. %, from 0.1 wt. % to 5.0 wt. %, from 0.1 wt. % to 2.5 wt. %, from 0.1 wt. % to 0.5 wt. %, from 0.5 wt. % to 10.0 wt. %, from 0.5 wt. % to 7.5 wt. %, from 0.5 wt. % to 5.0 wt. %, from 0.5 wt. % to 2.5 wt. %, from 2.5 wt. % to 10.0 wt. %, from 2.5 wt. % to 7.5 wt. %, from 2.5 wt. % to 5.0 wt. %, from 5.0 wt. % to 10.0 wt. %, from 5.0 wt. % to 7.5 wt. %, or from 7.5 wt. % to 10 wt. % gallium based on the total weight of the catalyst.

In one or more embodiments, the catalyst optionally includes less than 5 wt. % alkali metal or alkaline earth metal based on the total weight of the catalyst. For example, the catalyst may include from 0 wt. % to 5 wt. %, from 0 wt. % to 4 wt. %, from 0 wt. % to 3 wt. %, from 0 wt. % to 2 wt. %, from 0 wt. % to 1 wt. %, from 1 wt. % to 5 wt. %, from 1 wt. % to 4 wt. %, from 1 wt. % to 3 wt. %, from 1 wt. % to 2 wt. %, from 2 wt. % to 5 wt. %, from 2 wt. % to 4 wt. %, from 2 wt. % to 3 wt. %, from 3 wt. % to 5 wt. %, from 3 wt. % to 4 wt. %, or from 4 wt. % to 5 wt. % alkali metal or alkaline earth metal based on the total weight of the catalyst.

In one or more embodiments, the catalyst includes a support material. Specifically, the catalyst may include gallium, platinum, alkali metal, and/or alkaline earth metal disposed and/or dispersed on the support material. In some embodiments, the support material includes one or more of alumina, silica, titanium oxide, and zirconium. For example, the support material may include one or more of alumina, silica-containing alumina, titanium oxide-containing alumina, and zirconium-containing alumina.

Referring still to FIG. 1, the olefin-containing effluent and the catalyst may be passed out of the downstream reactor section 230 to a separation device 220 in the catalyst separation section 210. The catalyst may be separated from the olefin-containing effluent in the separation device 220. The olefin-containing effluent may then be transported out of the catalyst separation section 210. For example, the separated olefin-containing effluent may be removed from the reactor system 102 via a pipe 420 at a gas outlet port 216 of the catalyst separation section 210. In one or more embodiments, the separation device 220 may be a cyclonic separation system, which may include two or more stages of cyclonic separation.

Referring still to FIG. 1, following separation from the olefin-containing effluent in the separation device 220, the catalyst may generally move through the stripper 224 to the reactor catalyst outlet port 222 where the catalyst may be transferred out of the reactor portion 200 via standpipe 426 and into the combustor 350 of the catalyst-processing portion 300. Optionally, the catalyst may also be transferred directly back into the upstream reactor section 250 via standpipe 422. In one or more embodiments, recycled catalyst from the stripper 224 may be premixed with processed catalyst from the catalyst processing portion 300 in the transport riser 430.

Once passed to the catalyst-processing portion 300, the catalyst may be processed in the catalyst-processing portion 300. As used in the present disclosure, the term "catalyst processing" refers to preparing the catalyst for re-introduction into the reactor portion of the reactor system. In one or more embodiments, processing the catalyst includes removing coke deposits from the catalyst, raising the temperature of the catalyst through combustion of a combustion fuel, reactivating the catalyst, stripping one or more constituents from the catalyst, or combinations of these.

In some embodiments, processing the catalyst includes combusting the combustion fuel in the presence of the catalyst in the combustor 350 to remove coke deposits on the catalyst and/or heat the catalyst to produce a processed catalyst and combustion gases. As used in the present disclosure, the term "processed catalyst" refers to catalyst that has been processed in the catalyst-processing portion 300 of the reactor system 102. The processed catalyst may be separated from the combustion gases in the catalyst separation portion 310 and, in some embodiments, may then be reactivated by conducting an oxygen treatment of the heated catalyst. The oxygen treatment may include contacting the catalyst with an oxygen-containing gas for a period of time sufficient to reactivate the catalyst.

In one or more embodiments, the combustion fuel includes coke or other contaminants deposited on the catalyst in the reactor portion 200. The catalyst may be coked following the reactions in the reactor portion 200, and the coke may be removed from the catalyst by a combustion reaction in the combustor 350. For example, an oxidizer (such as air) may be fed into the combustor 350 via the air inlet 428. Alternatively or additionally, such as when coke is not formed on the catalyst or an amount of coke formed on the catalyst is not sufficient to burn off to heat the catalyst to a desired temperature, a supplemental fuel may be injected into the combustor 350, which may be burned to heat the catalyst. Suitable supplemental fuels may include methane, natural gas, ethane, propane, hydrogen, or any gas that provides energy value upon combustion.

The processed catalyst may be passed out of the combustor 350 and through the riser 330 to a riser termination separator 378, where the gas and solid components from the riser 330 may be at least partially separated. The vapor and remaining solids may be transported to a secondary separation device 320 in the catalyst separation section 310 where the remaining processed catalyst is separated from the gases from the catalyst processing (e.g., gases emitted by combustion of coke deposits and supplemental fuel). In some embodiments, the secondary separation device 320 may include one or a plurality of cyclone separation units, which may be arranged in series or in multiple cyclone pairs. The combustion gases from combustion of coke and/or the supplemental fuel during processing of the catalyst or other gases introduced to the catalyst during catalyst processing may be removed from the catalyst-processing portion 300 via a combustion gas outlet 432.

As previously discussed, processing the catalyst in the catalyst-processing portion 300 of the reactor system 102 may include reactivating the catalyst. Combustion of the supplemental fuel in the presence of the catalyst to heat the catalyst may further deactivate the catalyst. Accordingly, in some embodiments, the catalyst may be reactivated by conditioning the catalyst through an oxygen treatment. The oxygen treatment to reactivate the catalyst may be conducted after combustion of the supplemental fuel to heat the catalyst. In some embodiments, the oxygen treatment includes treating the processed catalyst with an oxygen-containing gas. The oxygen-containing gas may include an oxygen content of from 5 mole percent (mol. %) to 100 mol. % based on total molar flow rate of the oxygen-containing gas. In some embodiments, the oxygen treatment includes maintaining the processed catalyst at a temperature of at least 660 degrees Celsius (° C.) while exposing the catalyst to a flow of an oxygen-containing gas for a period of time sufficient to reactivate the processed catalyst (e.g., increase the catalytic activity of the processed catalyst).

In one or more embodiments, treatment of the processed catalyst with the oxygen-containing gas is conducted in the oxygen treatment zone 370. In some embodiments, the oxygen treatment zone 370 is downstream of the catalyst separation portion 310 of the catalyst-processing portion 300, such that the processed catalyst is separated from the combustion gases before being exposed to the oxygen-containing gas during the oxygen treatment. In some embodiments, the oxygen treatment zone 370 includes a fluid solids contacting device. The fluid solids contacting device may include baffles or grid structures to facilitate contact of the processed catalyst with the oxygen-containing gas. Examples of fluid solid contacting devices are described in further detail in U.S. Pat. Nos. 9,827,543 and 9,815,040.

In one or more embodiments, processing the catalyst in the catalyst-processing portion 300 of the reactor system 102 includes stripping the processed catalyst of molecular oxygen trapped within or between catalyst particles and physisorbed oxygen that is desorbable at a temperature of at least 660° C. The stripping step may include maintaining the processed catalyst at a temperature of at least 660° C. and exposing the processed catalyst to a stripping gas that is substantially free of molecular oxygen and combustible fuels for a period of time sufficient to remove the molecular oxygen from between particles and physisorbed oxygen that is desorbable at the temperature of at least 660° C. Further description of these catalyst reactivation processes are disclosed in U.S. Pat. No. 9,834,496.

Referring still to FIG. 1, following processing of the catalyst, the processed catalyst may be passed from the catalyst-processing portion 300 back into the reactor portion 200 via standpipe 424. For example, the processed catalyst may be passed from the oxygen treatment zone 370 to the upstream reactor section 250 via standpipe 424 and transport riser 430, where the processed catalyst may be further utilized in a dehydrogenation reaction of a hydrocarbon-containing feed. Accordingly, in operation, the catalyst may cycle between the reactor portion 200 and the catalyst-processing portion 300. In general, the processed chemical streams, including the hydrocarbon-containing feed and the olefin-containing effluent may be gaseous, and the catalyst may be a fluidized particulate solid. In one or more embodiments, the reactor system 102 may include a hydrogen inlet stream 480 which provides supplemental hydrogen to the reactor system 102.

As discussed previously, combustion reactions in the combustor 350 (i.e., the combustion of the combustion fuel) may be promoted by the catalyst. That is, the catalyst may provide combustion activity in the combustor 350. However, the combustion activity of the catalyst may decrease over time as the catalyst is cycled between the reactor portion 200 and the catalyst-processing portion 300. As a result, during operation of the reactor system 102, the combustion fuel may no longer combust at the typical operating temperatures and pressures of the combustor 350 without sufficient maintenance of combustion activity in the combustor 350. Typical operating temperatures of the combustor 305 maybe from 600° C. to 850° C., and typical operating pressures of the combustor 350 may be from 15 pounds per square inch absolute (psia) to 60 psia.

In one or more embodiments, the combustion activity in the combustor 350 may be sufficiently maintained by introducing a combustion additive to the reactor system 102. In some embodiments, the combustion additive is introduced to the reactor system 102 via the reactor portion 200, the catalyst-processing portion 300, or both. For example, the combustion additive may be introduced to the reactor system 102 via transport riser 430.

In some embodiments, the combustion additive includes catalytically active particles. In some embodiments, the combustion additive includes one or more of gallium, platinum, alkali metals, alkaline earth metals, and a support material. In some embodiments, the combustion additive may include the similar and/or the same materials as the catalyst. For example, in some embodiments both the catalyst and the combustion additive may include gallium and platinum disposed and/or dispersed on an alumina support material.

In one or more embodiments, the combustion additive includes from 150 ppmw to 1,000 ppmw platinum based on the total weight of the catalyst. For example, the combustion additive may include from 150 ppmw to 750 ppmw, from 150 ppmw to 500 ppmw, from 150 ppmw to 250 ppmw, from 150 ppmw to 200 ppmw, from 200 ppmw to 1,000 ppmw, from 200 ppmw to 750 ppmw, from 200 ppmw to 500 ppmw, from 200 ppmw to 250 ppmw, from 250 ppmw to 1,000 ppmw, from 250 ppmw to 750 ppmw, from 250 ppmw to 500 ppmw, from 500 ppmw to 1,000 ppmw, from 500 ppmw to 750 ppmw, or from 750 ppmw to 1,000 ppmw platinum based on the total weight of the combustion additive.

In one or more embodiments, the combustion additive includes at least 1.1 times greater platinum than the catalyst. For example, the combustion additive may include at least 1.5 times, at least 2 times, at least 5 times, at least 10 times, at least 20 times, or at least 50 times greater platinum than the catalyst. Without being bound by any particular theory, it is believed that the combustion activity of the catalyst and the combustion additive is mainly provided by platinum. While the catalyst generally includes sufficient amounts of accessible platinum to provide suitable combustion activity, the combustion activity of catalyst gradually decreases as discussed previously. Additionally, it is believed that increasing the amount of platinum does not correlate with increased retention of combustion activity. As a result, an increased amount of platinum on the catalyst, which may increase the economic costs of the FCDh process, may not provide a significant increase in either dehydrogenation activity or the ability of the catalyst to maintain suitable combustion activity for an increased period of time.

In one or more embodiments, the combustion additive includes from 0.1 wt. % to 10.0 wt. % gallium based on the total weight of the combustion additive. For example, the combustion additive may include from 0.1 wt. % to 7.5 wt. %, from 0.1 wt. % to 5.0 wt. %, from 0.1 wt. % to 2.5 wt. %, from 0.1 wt. % to 0.5 wt. %, from 0.5 wt. % to 10.0 wt. %, from 0.5 wt. % to 7.5 wt. %, from 0.5 wt. % to 5.0 wt. %, from 0.5 wt. % to 2.5 wt. %, from 2.5 wt. % to 10.0 wt. %, from 2.5 wt. % to 7.5 wt. %, from 2.5 wt. % to 5.0 wt. %, from 5.0 wt. % to 10.0 wt. %, from 5.0 wt. % to 7.5 wt. %, or from 7.5 wt. % to 10 wt. % gallium based on the total weight of the combustion additive.

In one or more embodiments, the combustion additive optionally includes less than 5 wt. % alkali metal or alkaline earth metal based on the total weight of the combustion additive. For example, the combustion additive may include from 0 wt. % to 5 wt. %, from 0 wt. % to 4 wt. %, from 0 wt. % to 3 wt. %, from 0 wt. % to 2 wt. %, from 0 wt. % to 1 wt. %, from 1 wt. % to 5 wt. %, from 1 wt. % to 4 wt. %, from 1 wt. % to 3 wt. %, from 1 wt. % to 2 wt. %, from 2 wt. % to 5 wt. %, from 2 wt. % to 4 wt. %, from 2 wt. % to 3 wt. %, from 3 wt. % to 5 wt. %, from 3 wt. % to 4 wt. %, or from 4 wt. % to 5 wt. % alkali metal or alkaline earth metal based on the total weight of the combustion additive.

In one or more embodiments, the combustion additive includes a support material. Specifically, the combustion additive may include gallium, platinum, alkali metal, and/or alkaline earth metal disposed and/or dispersed on the support material. In some embodiments, the support material includes one or more of alumina, silica, titanium oxide, and zirconium. For example, the support material may include one or more of alumina, silica-containing alumina, titanium oxide-containing alumina, and zirconium-containing alumina.

As discussed previously, the combustion additive may be introduced to the reactor system 102 to maintain a sufficient combustion activity in the combustor 350. In one or more embodiments, the combustion additive may be introduced to the reactor system 102 when the combustion gases (i.e., the gases produced by combusting the combustion fuel in the combustor 350) comprise one or more hydrocarbons (e.g., methane, ethane, and/or propane) in an amount greater than 5% of a lower flammability limit (LFL) of the combustion gases at a temperature and pressure of the catalyst-processing portion 300. For example, the combustion additive may be introduced to the reactor system 102 when the combustion gases comprise one or more hydrocarbons in an amount greater than 10% of the LFL of the combustion gases at a temperature and pressure of the catalyst-processing portion 300. As used in the present disclosure, the term "lower flammability limit" refers to the lower end of the concentration range over which a flammable mixture of gas or vapor in air can be ignited at a given temperature and pressure. The LFL of the combustion gases may be determined by reactive chemistry testing or as described by Michael G. Zabetakis, *Flammability Characteristics of Combustible Gases and Vapors*, 627 BUREAU OF MINES 1 (1965), with pressure adjustments according to Coward et al., *Limits of Flammability of Gases and Vapors*, 503 BUREAU OF MINES 1 (1952). It should be understood that while hydrogen may be used as a suitable supplemental fuel, as discussed previously, typical hydrogen sources may include some quantity of one or more hydrocarbons. Accordingly, even in embodiments where hydrogen is used as the combustion fuel, the combustion additive may be introduced to the reactor system 102 when the combustion gases include one or more hydrocarbons in an amount greater than 5% of the LFL of the combustion gases at a temperature and pressure of the catalyst-processing portion 300.

In one or more embodiments, the amount of the combustion additive introduced to the reactor system 102 is from 0.05 volume percent (vol. %) to 2 vol. % of a sum of a volume of the catalyst and a volume of the combustion additive. For example, the amount of the combustion additive introduced to the reactor system 102 may be from 0.05 vol. % to 1.5 vol. %, from 0.05 vol. % to 1 vol. %, from 0.05 vol. % to 0.5 vol. %, from 0.5 vol. % to 2 vol. %, from 0.5 vol. % to 1.5 vol. %, from 0.5 vol. % to 1 vol. %, from 1 vol. % to 2 vol. %, from 1 vol. % to 1.5 vol. %, or from 1.5 vol. % to 2 vol. % of a sum of a volume of the catalyst and a volume of the combustion additive.

It should be understood that, once introduced to the reactor system 102, the combustion additive will mix with the catalyst and, as a result, cycle through the reactor system 102 as discussed previously with regard to the catalyst. In other terms the introduction of the combustion additive to the reactor system 102 may produce a catalyst system that is a mixture of the catalyst and combustion additive. Additionally, as the catalyst system "ages" during use in the reactor system 102 and/or catalytically active particles are naturally lost due to attrition, the combustion additive and the catalyst may become indistinguishable from one another. In this regard, the catalyst system may become functionally equivalent to the original catalyst during operation of the reactor system 102, and fresh combustion additive may be again introduced to the reactor system 102. Due to the natural change in properties of the catalyst and combustion additive during operation of the reactor system 102, the properties and amounts of combustion additive and/or catalyst may refer to the properties and amounts of the combustion additive and/or catalyst upon introduction of the combustion additive to the reactor system 102.

In some embodiments, the catalyst system may include from 0.05 vol. % to 2 vol. % of the combustion additive. For example, catalyst system may include from 0.05 vol. % to 1.5 vol. %, from 0.05 vol. % to 1 vol. %, from 0.05 vol. % to 0.5 vol. %, from 0.5 vol. % to 2 vol. %, from 0.5 vol. % to 1.5 vol. %, from 0.5 vol. % to 1 vol. %, from 1 vol. % to 2 vol. %, from 1 vol. % to 1.5 vol. %, or from 1.5 vol. % to 2 vol. % of the combustion additive. In some embodiments, the catalyst system may include from 98 vol. % to 99.95 vol. % of the catalyst. For example, catalyst system may include from 98 vol. % to 99.5 vol. %, from 98 vol. % to 99 vol. %, from 98 vol. % to 98.5 vol. %, from 98.5 vol. % to 99.95 vol. %, from 98.5 vol. % to 99.5 vol. %, from 98.5 vol. % to 99 vol. %, from 99 vol. % to 99.95 vol. %, from 99 vol. % to 99.5 vol. %, or from 99.5 vol. % to 99.95 vol. % of the catalyst.

EXAMPLES

The various embodiments of the present disclosure will be further clarified by the following examples. The examples are illustrative in nature and should not be understood to limit the subject matter of the present disclosure.

Example 1

In Example 1, seven different samples of catalytically active particles (i.e., catalysts and/or combustion additives) were prepared. For the purposes of Example 1, the amount of gallium and potassium loading of each sample was constant at 1.6 wt. % and 0.25 wt. %, respectively, while the amount of platinum loading of each sample was varied. Each sample was produced by loading an alumina support material with platinum, potassium, and, optionally, gallium via a conventional incipient wetness impregnation method, as described in Marceau et al., *Impregnation and Drying*, SYNTHESIS OF SOLID CATALYSTS 59 (2008). The platinum loading of each sample is reported in Table 1.

TABLE 1

| Catalytically Active Particles | Platinum Loading (ppm) |
|---|---|
| Sample A | 25 |
| Sample B | 50 |
| Sample C | 100 |
| Sample D | 200 |
| Sample E | 300 |
| Sample F | 500 |
| Sample G | 0 |
| Sample H[1] | 200 |

[1]Sample H did not include gallium.

Example 2

In Example 2, the effect various properties, such as platinum loading, of catalytically active particles have on dehydrogenation activity were examined. In order to simulate the aging of catalytically active particles in a large scale fluidized catalytic dehydrogenation system, some samples were subjected to an aging protocol. Specifically, Samples A-C were subjected to four high temperature treatment-jet treatment cycles (also referred to as "Protocol I"). Each cycle included a 10-hour treatment under air at 750° C. followed by a 48-hour treatment under a nitrogen-jet with a jet velocity of 300 ft/s. The jet treatments were conducted in a pilot jet cup attrition facility, as described in Cocco et al., *Jet Cup Attrition Testing*, 200 Powder Technology 224 (2010).

Next, fresh and aged versions of some samples were tested for dehydrogenation activity. Specifically, dehydrogenation testing was carried out in a fixed-bed rig under lab simulated reaction-regeneration cycles. Each reaction cycle was conducted at 625° C. for 60 seconds with a WHSV of 8 $hr^{-1}$ and a feed composition of 95% propane/5% nitrogen. Each regeneration cycle was conducted under air at 750° C. for 15 minutes. Data for each run was collected at 15 seconds on stream. The results from cycle 15 of each run are reported in Table 2. It should be noted that all reported indices are based on performance normalized with that of Sample B.

TABLE 2

| | Fresh Sample | | Aged Sample (Protocol I) | | |
|---|---|---|---|---|---|
| Sample | Conversion Rate (mol-Propane/g-Catalyst/hr) | Dehydrogenation Activity Index | Conversion Rate (mol-Propane/g-Catalyst/hr) | Dehydrogenation Activity Index | Activity Retention (Aged/Fresh) |
| Sample A | 1.77 | 1.04 | 1.77 | 1.00 | 100% |
| Sample B | 1.70 | 1.00 | 1.78 | 1.00 | 105% |
| Sample C | 1.72 | 1.01 | 1.74 | 0.98 | 101% |
| Sample D | 1.80 | 1.06 | — | — | — |
| Sample G | 1.35 | 0.80 | — | — | — |
| Sample H | 0.55 | 0.32 | — | — | — |

As indicated by Table 2, samples without gallium (i.e., Sample H) provided only limited dehydrogenation activity. In contrast, samples with gallium and without platinum (i.e., Sample G) provided suitable dehydrogenation activity. Further, the addition of relatively minor amounts of platinum to catalytically active particles including gallium enhanced the dehydrogenation activity of the catalytically active particles significantly, as indicated by a comparison of Samples A and G. However, Table 2 indicates that further increases in the amount of platinum did not further increase dehydrogenation activity, as indicated by a comparison of Samples A-D.

Example 3

In Example 3, the effect various properties, such as platinum loading, of catalytically active particles have on combustion activity were examined. In order to simulate the aging of catalytically active particles in a large scale fluidized catalytic dehydrogenation system, some samples were subjected to an aging protocol. Specifically, Samples B-F and H were subjected to six high temperature treatment-jet treatment cycles (also referred to as "Protocol II"). Each cycle was conducted in a manner similar to Protocol I, as described in Example 2, but the heat treatments were conducted for 48 hours, and the jet treatments were conducted for with a jet velocity of 150 ft/s for 6 hours.

Next, fresh and aged versions of some samples were tested for combustion activity. Specifically, combustion testing was carried out in a fixed-bed testing rig under 2 mol. % methane in air at 750° C. for 100 minutes. The results of each run are reported in Table 3. It should be noted that all reported indices are based on performance normalized with that of Sample B.

TABLE 3

| Sample | Fresh Sample | | Aged Sample (Protocol II) | | Activity Retention (Aged/Fresh) |
| --- | --- | --- | --- | --- | --- |
| | Conversion Rate (mol-Methane/g-Catalyst/hr) | Combustion Activity Index | Conversion Rate (mol-Methane/g-Catalyst/hr) | Combustion Activity Index | |
| Sample B | 0.0103 | 1.00 | 0.0086 | 1.00 | 84% |
| Sample C | 0.0105 | 1.02 | 0.0089 | 1.03 | 85% |
| Sample D | 0.0111 | 1.08 | 0.0085 | 0.99 | 77% |
| Sample E | 0.0129 | 1.26 | 0.0096 | 1.11 | 74% |
| Sample F | 0.0172 | 1.68 | 0.0103 | 1.19 | 59% |
| Sample H | 0.0086 | 0.89 | — | — | — |

As indicated by Table 3, samples with increased platinum loading provided increased combustion activity. However, samples with increased platinum loading also had a poorer activity retention. That is, Table 3 indicates that increased platinum loading of catalytically active particles will not necessarily result in a corresponding increase in the duration the catalytically active particles maintain a suitable combustion activity. Put more simply, Table 3 indicates that increasing the amount of platinum loading by 50% will not necessarily increase the duration the catalytically active particles maintain a suitable combustion activity by 50%.

Several aspects are disclosed herein. One aspect is a method for producing olefins, the method comprising: contacting a hydrocarbon-containing feed with a catalyst in a reactor portion of a reactor system to form an olefin-containing effluent; separating at least a portion of the olefin-containing effluent from the catalyst; passing the catalyst to a catalyst-processing portion of the reactor system and processing the catalyst to produce a processed catalyst and a combustion gas; passing the processed catalyst from the catalyst processing portion to the reactor portion; and introducing a combustion additive to the reactor system when the combustion gas comprises one or more hydrocarbons in an amount greater than 5% of a lower flammability level of the combustion gas at a temperature and pressure of the catalyst-processing portion, wherein: the catalyst comprises from 1 parts per million by weight to 150 parts per million by weight platinum; and the combustion additive comprises from 150 parts per million by weight to 1,000 parts per million by weight platinum.

Another aspect is any other aspect disclosed herein, wherein the catalyst further comprises gallium and a support material.

Another aspect is any other aspect disclosed herein, wherein the catalyst comprises from 0.1 weight percent to 10.0 weight percent gallium.

Another aspect is any other aspect disclosed herein, wherein the support material comprises alumina, silica, titanium oxide, or zirconium.

Another aspect is any other aspect disclosed herein, wherein the catalyst further comprises less than or equal to 5 weight percent alkali metal or alkaline earth metal.

Another aspect is any other aspect disclosed herein, wherein the combustion additive further comprises gallium and a support material.

Another aspect is any other aspect disclosed herein, wherein the combustion additive comprises from 0.1 weight percent to 10.0 weight percent gallium.

Another aspect is any other aspect disclosed herein, wherein the support material comprises alumina, silica, titanium oxide, or zirconium.

Another aspect is any other aspect disclosed herein, wherein the combustion additive further comprises less than or equal to 5 weight percent alkali metal or alkaline earth metal.

Another aspect is any other aspect disclosed herein, wherein processing the catalyst comprises combusting a supplemental fuel in the catalyst-processing portion to heat the catalyst.

Another aspect is any other aspect disclosed herein, wherein the supplemental fuel comprises methane, natural gas, ethane, propane, or hydrogen.

Another aspect is any other aspect disclosed herein, wherein processing the catalyst comprises contacting the catalyst with an oxygen-containing gas.

Another aspect is any other aspect disclosed herein, wherein the combustion additive is introduced to the reactor portion, the catalyst-processing portion, or both.

Another aspect is any other aspect disclosed herein, wherein the amount of the combustion additive introduced to the reactor system is from 0.05 volume percent to 2 volume percent of a sum of a volume of the catalyst and a volume of the combustion additive.

Another aspect is any other aspect disclosed herein, wherein the combustion additive comprises at least 1.1 times greater platinum than the catalyst.

The dimensions and values presently disclosed are not to be understood as being strictly limited to the exact numerical values recited. Instead, unless otherwise specified, each such dimension or value is intended to mean both the recited value and a functionally equivalent range surrounding that value. For example, a value disclosed as "150 ppmw" is intended to mean "about 150 ppmw."

Every document cited in the present disclosure, if any, including any cross-referenced or related patent or patent application, and any patent or patent application to which this application claims priority or benefit, is incorporated by reference in its entirety unless expressly excluded or otherwise limited. The citation of any document is not an admission that it is prior art with respect to any embodiment disclosed or claimed, or that it alone, or in any combination with any other reference or references, teaches, suggests, or discloses any such embodiment. Further, to the extent that any meaning or definition of a term in this document conflicts with any meaning or definition of the same term in a document incorporated by reference, the meaning or definition assigned to that term in this document govern21s.

It is noted that one or more of the following claims utilize the term "wherein" as a transitional phrase. For the purposes of defining the embodiments of the present disclosure, it is noted that this term is introduced in the claims as an open-ended transitional phrase that is used to introduce a recitation of a series of characteristics of the embodiment and should be interpreted in like manner as the more commonly used open-ended preamble term "comprising."

It will be apparent to those skilled in the art that various modifications and variations can be made to the presently disclosed embodiments without departing from the scope of the present disclosure. Since modifications, combinations, sub-combinations, and variations of the presently disclosed embodiments incorporating scope of the present disclosure may occur to persons of ordinary skill in the art, the present disclosure should be construed to include everything within the scope of the appended claims and their equivalents.

The invention claimed is:

1. A method for producing olefins, the method comprising:
    contacting a hydrocarbon-containing feed with a catalyst in a reactor portion of a reactor system to form an olefin-containing effluent;
    separating at least a portion of the olefin-containing effluent from the catalyst;
    passing the catalyst to a catalyst-processing portion of the reactor system and processing the catalyst to produce a processed catalyst and a combustion gas;
    passing the processed catalyst from the catalyst processing portion to the reactor portion; and
    introducing a combustion additive to the reactor system when the combustion gas comprises one or more hydrocarbons in an amount greater than 5% of a lower flammability level of the combustion gas at a temperature and pressure of the catalyst-processing portion, wherein:
    the catalyst comprises from 1 parts per million by weight to 150 parts per million by weight platinum; and
    the combustion additive comprises from 150 parts per million by weight to 1,000 parts per million by weight platinum.

2. The method of claim 1, wherein the catalyst further comprises gallium and a support material.

3. The method of claim 2, wherein the catalyst comprises from 0.1 weight percent to 10.0 weight percent gallium.

4. The method of claim 2, wherein the support material comprises alumina, silica, titanium oxide, or zirconium.

5. The method of claim 1, wherein the catalyst further comprises less than or equal to 5 weight percent alkali metal or alkaline earth metal.

6. The method of claim 1, wherein the combustion additive further comprises gallium and a support material.

7. The method of claim 6, wherein the combustion additive comprises from 0.1 weight percent to 10.0 weight percent gallium.

8. The method of claim 6, wherein the support material comprises alumina, silica, titanium oxide, or zirconium.

9. The method of claim 1, wherein the combustion additive further comprises less than or equal to 5 weight percent alkali metal or alkaline earth metal.

10. The method of claim 1, wherein processing the catalyst comprises combusting a supplemental fuel in the catalyst-processing portion to heat the catalyst.

11. The method of claim 10, wherein the supplemental fuel comprises methane, natural gas, ethane, propane, or hydrogen.

12. The method of claim 1, wherein processing the catalyst comprises contacting the catalyst with an oxygen-containing gas.

13. The method of claim 1, wherein the combustion additive is introduced to the reactor portion, the catalyst-processing portion, or both.

14. The method of claim 1, wherein the amount of the combustion additive introduced to the reactor system is from 0.05 volume percent to 2 volume percent of a sum of a volume of the catalyst and a volume of the combustion additive.

15. The method of claim 1, wherein the combustion additive comprises at least 1.1 times greater platinum than the catalyst.

* * * * *